United States Patent
Bingham et al.

(10) Patent No.: US 6,277,979 B1
(45) Date of Patent: Aug. 21, 2001

(54) KIAA0551 POLYNUCLEOTIDES AND POLYPEPTIDES USE

(75) Inventors: Sharon Bingham, Saffron Walden; Patrick Case, Bristol; Sally Neale Lawson, Bristol; Richard Anthony Newton, Bristol; Oliver Lars Rausch, London; Alastair David Reith, Barnet; Gareth John Sanger, Sawbridgeworth, all of (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 09/393,569

(22) Filed: Sep. 10, 1999

(30) Foreign Application Priority Data

Sep. 10, 1998 (GB) .................................... 9819779
Mar. 29, 1999 (GB) .................................... 9907261

(51) Int. Cl.⁷ .......................... C07H 21/04; C12N 15/63; C12N 5/00; C12N 15/00
(52) U.S. Cl. .................... 536/23.5; 536/23.1; 435/320.1; 435/325; 435/69.1
(58) Field of Search ................................ 435/320.1, 325, 435/180, 455, 69.1; 530/350, 300; 536/23.1, 23.5

(56) References Cited

PUBLICATIONS

GenCore Accession No. O60298, Nagase et al., Aug. 1998.*

GenCore Accession No. AB011123, Ohara et al., Apr. 1998.*

Leube et al. J of Cell Biology, 127(6): 1589–1601, Dec. 1994.*

* cited by examiner

Primary Examiner—Scott D. Priebe
Assistant Examiner—Ram R. Shukla
(74) Attorney, Agent, or Firm—William T. Han; Ratner & Prestia; William T. King

(57) ABSTRACT

The use of KIAA0551 polypeptides and polynucleotides in the design of protocols for the treatment of neuropathies, neuropathic pain, inflammatory and chronic pain, neurodegenerative conditions such as Motor Neuron Disease, Parkinson's Disease, Alzheimer's Disease and other dementias, as well as ischaemic damage in neuronal and cardiac tissues, through disease or infectious agents, among others, and diagnostic assays for such conditions. Also disclosed are methods for producing such polypeptides by recombinant techniques.

5 Claims, 6 Drawing Sheets

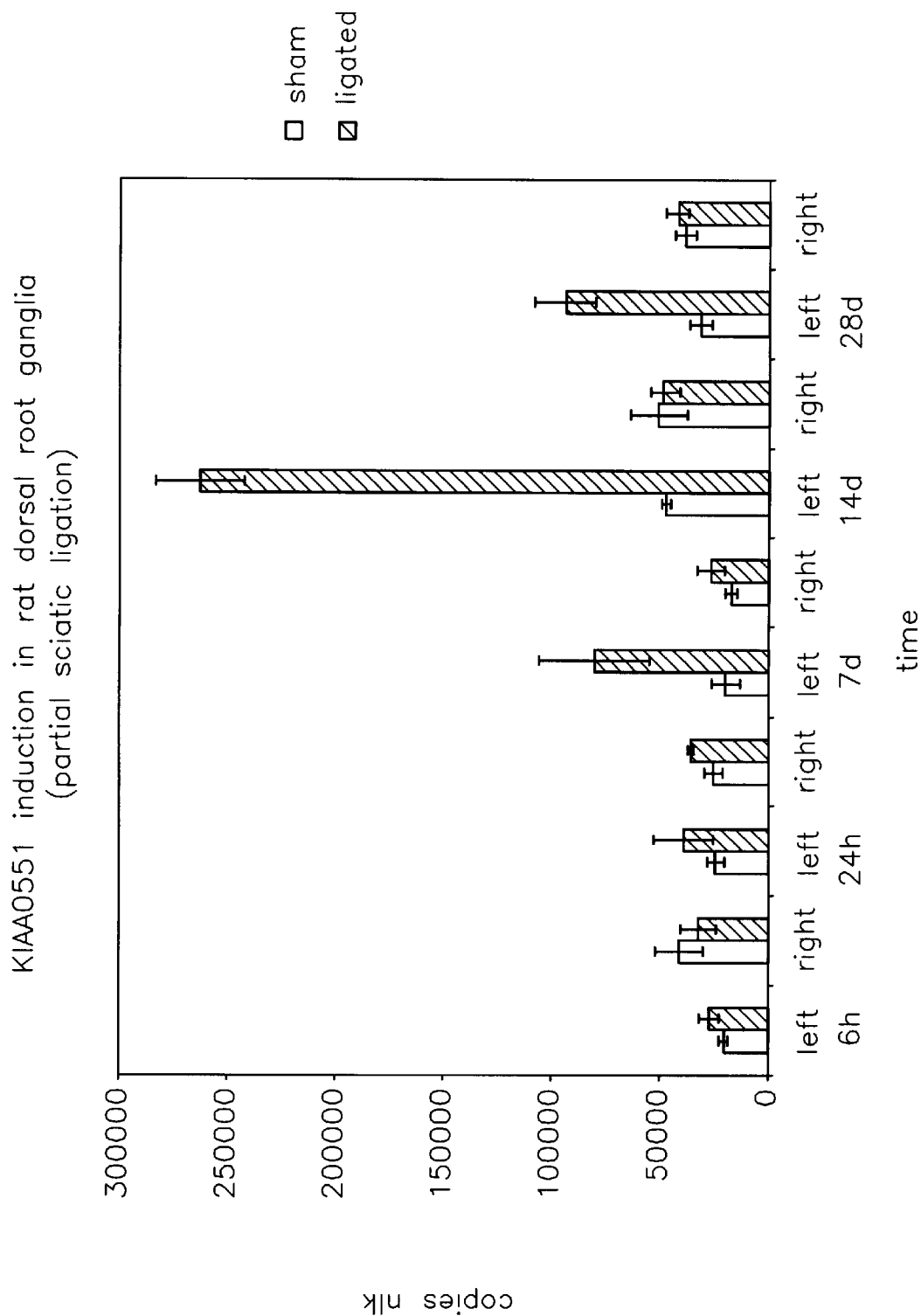

SEQUENCE LISTING

```
<160> NUMBER OF SEQ ID NOS: 5

<210> SEQ ID NO 1
<211> LENGTH: 4181
<212> TYPE: DNA
<213> ORGANISM: HOMO SAPIENS

<400> SEQUENCE: 1
cacccgcatg aggacgcgag tgaaatagac caaggtggaa tttccaaggg aaaagcttcg     60
gggtggtttt ggtccatttc tccagcgaag aagtagacat ggcgagcgac tccccggctc    120
gaagcctgga tgaaatagat ctctcggctc tgagggaccc tgcagggatc tttgaattgg    180
tggaacttgt tggaaatgga acatacgggc aagtttataa gggtcgtcat gtcaaaacgg    240
gccagcttgc agccatcaag gttatggatg tcacagggga tgaagaggaa gaaatcaaac    300
aagaaattaa catgttgaag aaatattctc atcaccggaa tattgctaca tactatggtg    360
cttttatcaa aaagaaccca ccaggcatgg atgaccaact ttggttggtg atggagtttt    420
```

```
gtggtgctgg ctctgtcacc gacctgatca agaacacaaa aggtaacacg ttgaaagagg    480
agtggattgc atacatctgc agggaaatct tacgggggct gagtcacctg caccagcata    540
aagtgattca tcgagatatt aaagggcaaa atgtcttgct gactgaaaat gcagaagtta    600
aactagtgga cttttggagtc agtgctcagc ttgatcgaac agtgggcagg aggaatactt    660
tcattggaac tccctactgg atggcaccag aagttattgc ctgtgatgaa acccagatg     720
ccacatatga tttcaagagt gacttgtggt ctttgggtat caccgccatt gaaatggcag    780
aaggtgctcc ccctctctgt gacatgcacc ccatgagagc tctcttcctc atcccccgga    840
atccagcgcc tcggctgaag tctaagaagt ggtcaaaaaa attccagtca tttattgaga    900
gctgcttggt aaagaatcac agccagcgac cagcaacaga acaattgatg aagcatccat    960
ttatacgaga ccaacctaat gagcgacagg tccgcattca actcaaggac catattgata   1020
gaacaaagaa gaagcgagga gaaaaagatg agacagagta tgagtacagt ggaagtgagg   1080
aagaagagga ggagaatgac tcaggagagc ccagctccat cctgaatctg ccaggggagt   1140
cgacgctgcg gagggacttt ctgaggctgc agctggccaa caaggagcgt tctgaggccc   1200
tacggaggca gcagctggag cagcagcagc gggagaatga ggagcacaag cggcagctgc   1260
tggccgagcg tcagaagcgc atcgaggagc agaaagagca gaggcggcgg ctggaggagc   1320
aacaaaggcg agagaaggag ctgcggaagc agcaggagag ggagcagcgc cggcactatg   1380
aggagcagat gcgccgggag gaggagagga ggcgtgcgga gcatgaacag gaatacatca   1440
ggcgacagtt agaggaggag cagagacagt tagagatctt gcagcagcag ctactgcatg   1500
aacaagctct acttctggaa tataagcgca acaattggga gaacagaga caagcagaaa   1560
gactgcagag gcagctaaag caagaaagag actacttagt ttcccttcag catcagcggc   1620
aggagcagag gcctgtggag aagaagccac tgtaccatta caaagaagga atgagtccta   1680
gtgagaagcc agcatgggcc aaggaggtag aagaacggtc aaggctcaac cggcaaagtt   1740
cccctgccat gcctcacaag gttgccaaca ggatatctga ccccaacctg cccccaaggt   1800
cggagtcctt cagcattagt ggagttcagc ctgctcgaac acccccatg ctcagaccag    1860
tcgatcccca gatcccacat ctggtagctg taaaatccca gggacctgcc ttgaccgcct   1920
cccagtcagt gcacgagcag cccacaaagg gcctctctgg gtttcaggag gctctgaacg   1980
tgacctccca ccgcgtggag atgccacgcc agaactcaga tcccacctcg gaaaatcctc   2040
ctctccccac tcgcattgaa aagtttgacc gaagctcttg gttacgacag gaagaagaca   2100
ttccaccaaa ggtgcctcaa agaacaactt ctatatcccc agcattagcc agaaagaatt   2160
ctcctgggaa tggtagtgct ctgggaccca gactaggatc tcaacccatc agagcaagca   2220
accctgatct ccggagaact gagcccatct tggagagccc cttgcagagg accagcagtg   2280
gcagttcctc cagctccagc acccctagct cccagcccag ctcccaagga ggctcccagc   2340
ctggatcaca agcaggatcc agtgaacgca ccagagttcg agccaacagt aagtcagaag   2400
gatcacctgt gcttccccat gagcctgcca aggtgaaacc agaagaatcc agggacatta   2460
cccggcccag tcgaccagct agctacaaaa aagctataga tgaggatctg acggcattag   2520
ccaaagaact aagagaactc cggattgaag aaacaaaccg cccaatgaag aaggtgactg   2580
attactcctc ctccagtgag gagtcagaaa gtagcgagga agaggaggaa gatggagaga   2640
gcgagaccca tgatgggaca gtggctgtca gcgacatacc cagactgata ccaacaggag   2700
ctccaggcag caacgagcag tacaatgtgg gaatggtggg gacgcatggg ctggagacct   2760
```

| | | | | |
|---|---|---|---|---|
| ctcatgcgga | cagtttcagc | ggcagtattt | caagagaagg | aaccttgatg attagagaga | 2820 |
| cgtctggaga | gaagaagcga | tctggccaca | gtgacagcaa | tggctttgct ggccacatca | 2880 |
| acctccctga | cctggtgcag | cagagccatt | ctccagctgg | aaccccgact gagggactgg | 2940 |
| ggcgcgtctc | aacccattcc | caggagatgg | actctgggac | tgaatatggc atggggagca | 3000 |
| gcaccaaagc | ctccttcacc | ccctttgtgg | acccagagt | ataccagacg tctcccactg | 3060 |
| atgaagatga | agaggatgag | gaatcatcag | ccgcagctct | gtttactagc gaacttctta | 3120 |
| ggcaagaaca | ggccaaactc | aatgaagcaa | gaaagatttc | ggtggtaaat gtaaacccaa | 3180 |
| ccaacattcg | gcctcatagc | gacacaccag | aaatcagaaa | atacaagaaa cgattcaact | 3240 |
| cagaaatact | ttgtgcagct | ctgtggggtg | taaaccttct | ggtggggact gaaaatggcc | 3300 |
| tgatgctttt | ggaccgaagt | gggcaaggca | agtctataa | tctgatcaac cggaggcgat | 3360 |
| ttcagcagat | ggatgtgcta | gagggactga | atgtccttgt | gacaatttca ggaaagaaga | 3420 |
| ataagctacg | agtttactat | ctttcatggt | taagaaacag | aatactacat aatgacccag | 3480 |
| aagtagaaaa | gaaacaaggc | tggatcactg | ttggggactt | ggaaggctgt atacattata | 3540 |
| aagttgttaa | atatgaaagg | atcaaatttt | tggtgattgc | cttaaagaat gctgtggaaa | 3600 |
| tatatgcttg | ggctcctaaa | ccgtatcata | aattcatggc | atttaagtct tttgcagatc | 3660 |
| tccagcacaa | gcctctgcta | gttgatctca | cggtagaaga | aggtcaaaga ttaaaggtta | 3720 |
| tttttggttc | acacactggt | ttccatgtaa | ttgatgttga | ttcaggaaac tcttatgata | 3780 |
| tctacatacc | atctcatatt | caggcaata | tcactcctca | tgctattgtc atcttgccta | 3840 |
| aaacagatgg | aatggaaatg | cttgtttgct | atgaggatga | gggggtgtat gtaaacacct | 3900 |
| atggccggat | aactaaggat | gtggtgctcc | aatggggaga | atgcccacg tctgtggcct | 3960 |
| acattcattc | caatcagata | atgggctggg | gcgagaaagc | tattgagatc cggtcagtgg | 4020 |
| aaacaggaca | tttggatgga | gtatttatgc | ataagcgagc | tcaaaggtta aagtttctat | 4080 |
| gtgaaagaaa | tgataaggta | tttttgcat | ccgtgcgatc | tggaggaagt agccaagtgt | 4140 |
| tttcatgac | cctcaacaga | aattccatga | tgaactggta | a | 4181 |

<210> SEQ ID NO 2
<211> LENGTH: 1360
<212> TYPE: PRT
<213> ORGANISM: HOMO SAPIENS

<400> SEQUENCE: 2

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Gly Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Asn Pro Pro Gly
            85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
            115                 120                 125

```
Trp Ile Ala Tyr Ile Cys Arg Glu Ile Leu Arg Gly Leu Ser His Leu
    130                 135                 140
His Gln His Lys Val Ile His Arg Asp Ile Lys Gly Gln Asn Val Leu
145                 150                 155                 160
Leu Thr Glu Asn Ala Glu Val Lys Leu Val Asp Phe Gly Val Ser Ala
                165                 170                 175
Gln Leu Asp Arg Thr Val Gly Arg Arg Asn Thr Phe Ile Gly Thr Pro
            180                 185                 190
Tyr Trp Met Ala Pro Glu Val Ile Ala Cys Asp Glu Asn Pro Asp Ala
        195                 200                 205
Thr Tyr Asp Phe Lys Ser Asp Leu Trp Ser Leu Gly Ile Thr Ala Ile
    210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Ala Pro Arg Leu Lys Ser Lys
                245                 250                 255
Lys Trp Ser Lys Lys Phe Gln Ser Phe Ile Glu Ser Cys Leu Val Lys
            260                 265                 270
Asn His Ser Gln Arg Pro Ala Thr Glu Gln Leu Met Lys His Pro Phe
        275                 280                 285
Ile Arg Asp Gln Pro Asn Glu Arg Gln Val Arg Ile Gln Leu Lys Asp
    290                 295                 300
His Ile Asp Arg Thr Lys Lys Arg Gly Glu Lys Asp Glu Thr Glu
305                 310                 315                 320
Tyr Glu Tyr Ser Gly Ser Glu Glu Glu Glu Glu Asn Asp Ser Gly
                325                 330                 335
Glu Pro Ser Ser Ile Leu Asn Leu Pro Gly Glu Ser Thr Leu Arg Arg
            340                 345                 350
Asp Phe Leu Arg Leu Gln Leu Ala Asn Lys Glu Arg Ser Glu Ala Leu
        355                 360                 365
Arg Arg Gln Gln Leu Glu Gln Gln Arg Glu Asn Glu Glu His Lys
370                 375                 380
Arg Gln Leu Leu Ala Glu Arg Gln Lys Arg Ile Glu Glu Gln Lys Glu
385                 390                 395                 400
Gln Arg Arg Arg Leu Glu Glu Gln Gln Arg Arg Glu Lys Glu Leu Arg
                405                 410                 415
Lys Gln Gln Glu Arg Glu Gln Arg Arg His Tyr Glu Glu Gln Met Arg
            420                 425                 430
Arg Glu Glu Arg Arg Arg Ala Glu His Glu Gln Glu Tyr Ile Arg
        435                 440                 445
Arg Gln Leu Glu Glu Glu Gln Arg Gln Leu Glu Ile Leu Gln Gln Gln
    450                 455                 460
Leu Leu His Glu Gln Ala Leu Leu Leu Glu Tyr Lys Arg Lys Gln Leu
465                 470                 475                 480
Glu Glu Gln Arg Gln Ala Glu Arg Leu Gln Arg Gln Leu Lys Gln Glu
                485                 490                 495
Arg Asp Tyr Leu Val Ser Leu Gln His Gln Arg Gln Glu Gln Arg Pro
            500                 505                 510
Val Glu Lys Lys Pro Leu Tyr His Tyr Lys Glu Gly Met Ser Pro Ser
        515                 520                 525
Glu Lys Pro Ala Trp Ala Lys Glu Val Glu Glu Arg Ser Arg Leu Asn
530                 535                 540
```

```
Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
            565                 570                 575

Gln Pro Ala Arg Thr Pro Pro Met Leu Arg Pro Val Asp Pro Gln Ile
            580                 585                 590

Pro His Leu Val Ala Val Lys Ser Gln Gly Pro Ala Leu Thr Ala Ser
            595                 600                 605

Gln Ser Val His Glu Gln Pro Thr Lys Gly Leu Ser Gly Phe Gln Glu
            610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
            645                 650                 655

Asp Arg Ser Ser Trp Leu Arg Gln Glu Glu Asp Ile Pro Pro Lys Val
            660                 665                 670

Pro Gln Arg Thr Thr Ser Ile Ser Pro Ala Leu Ala Arg Lys Asn Ser
            675                 680                 685

Pro Gly Asn Gly Ser Ala Leu Gly Pro Arg Leu Gly Ser Gln Pro Ile
            690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Thr Pro
            725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
            755                 760                 765

Ser Pro Val Leu Pro His Glu Pro Ala Lys Val Lys Pro Glu Glu Ser
770                 775                 780

Arg Asp Ile Thr Arg Pro Ser Arg Pro Ala Ser Tyr Lys Lys Ala Ile
785                 790                 795                 800

Asp Glu Asp Leu Thr Ala Leu Ala Lys Glu Leu Arg Glu Leu Arg Ile
            805                 810                 815

Glu Glu Thr Asn Arg Pro Met Lys Lys Val Thr Asp Tyr Ser Ser Ser
            820                 825                 830

Ser Glu Glu Ser Glu Ser Ser Glu Glu Glu Glu Asp Gly Glu Ser
            835                 840                 845

Glu Thr His Asp Gly Thr Val Ala Val Ser Asp Ile Pro Arg Leu Ile
850                 855                 860

Pro Thr Gly Ala Pro Gly Ser Asn Glu Gln Tyr Asn Val Gly Met Val
865                 870                 875                 880

Gly Thr His Gly Leu Glu Thr Ser His Ala Asp Ser Phe Ser Gly Ser
            885                 890                 895

Ile Ser Arg Glu Gly Thr Leu Met Ile Arg Glu Thr Ser Gly Glu Lys
            900                 905                 910

Lys Arg Ser Gly His Ser Asp Ser Asn Gly Phe Ala Gly His Ile Asn
            915                 920                 925

Leu Pro Asp Leu Val Gln Gln Ser His Ser Pro Ala Gly Thr Pro Thr
            930                 935                 940

Glu Gly Leu Gly Arg Val Ser Thr His Ser Gln Glu Met Asp Ser Gly
945                 950                 955                 960

Thr Glu Tyr Gly Met Gly Ser Ser Thr Lys Ala Ser Phe Thr Pro Phe
```

-continued

```
                   965                 970                 975
Val Asp Pro Arg Val Tyr Gln Thr Ser Pro Thr Asp Glu Asp Glu
                980                 985                 990
Asp Glu Glu Ser Ser Ala Ala Leu Phe Thr Ser Glu Leu Leu Arg
                995                1000                1005
Gln Glu Gln Ala Lys Leu Asn Glu Ala Arg Lys Ile Ser Val Val Asn
           1010                1015                1020
Val Asn Pro Thr Asn Ile Arg Pro His Ser Asp Thr Pro Glu Ile Arg
1025                1030                1035                104
Lys Tyr Lys Lys Arg Phe Asn Ser Glu Ile Leu Cys Ala Ala Leu Trp
                1045                1050                1055
Gly Val Asn Leu Leu Val Gly Thr Glu Asn Gly Leu Met Leu Leu Asp
                1060                1065                1070
Arg Ser Gly Gln Gly Lys Val Tyr Asn Leu Ile Asn Arg Arg Arg Phe
                1075                1080                1085
Gln Gln Met Asp Val Leu Glu Gly Leu Asn Val Leu Val Thr Ile Ser
                1090                1095                1100
Gly Lys Lys Asn Lys Leu Arg Val Tyr Tyr Leu Ser Trp Leu Arg Asn
1105                1110                1115                112
Arg Ile Leu His Asn Asp Pro Glu Val Glu Lys Lys Gln Gly Trp Ile
                1125                1130                1135
Thr Val Gly Asp Leu Glu Gly Cys Ile His Tyr Lys Val Val Lys Tyr
                1140                1145                1150
Glu Arg Ile Lys Phe Leu Val Ile Ala Leu Lys Asn Ala Val Glu Ile
                1155                1160                1165
Tyr Ala Trp Ala Pro Lys Pro Tyr His Lys Phe Met Ala Phe Lys Ser
                1170                1175                1180
Phe Ala Asp Leu Gln His Lys Pro Leu Leu Val Asp Leu Thr Val Glu
1185                1190                1195                120
Glu Gly Gln Arg Leu Lys Val Ile Phe Gly Ser His Thr Gly Phe His
                1205                1210                1215
Val Ile Asp Val Asp Ser Gly Asn Ser Tyr Asp Ile Tyr Ile Pro Ser
                1220                1225                1230
His Ile Gln Gly Asn Ile Thr Pro His Ala Ile Val Ile Leu Pro Lys
                1235                1240                1245
Thr Asp Gly Met Glu Met Leu Val Cys Tyr Glu Asp Glu Gly Val Tyr
                1250                1255                1260
Val Asn Thr Tyr Gly Arg Ile Thr Lys Asp Val Val Leu Gln Trp Gly
1265                1270                1275                128
Glu Met Pro Thr Ser Val Ala Tyr Ile His Ser Asn Gln Ile Met Gly
                1285                1290                1295
Trp Gly Glu Lys Ala Ile Glu Ile Arg Ser Val Glu Thr Gly His Leu
                1300                1305                1310
Asp Gly Val Phe Met His Lys Arg Ala Gln Arg Leu Lys Phe Leu Cys
                1315                1320                1325
Glu Arg Asn Asp Lys Val Phe Phe Ala Ser Val Arg Ser Gly Gly Ser
                1330                1335                1340
Ser Gln Val Phe Phe Met Thr Leu Asn Arg Asn Ser Met Met Asn Trp
1345                1350                1355                1360
```

<210> SEQ ID NO 3
<211> LENGTH: 424
<212> TYPE: DNA
<213> ORGANISM: HOMO SAPIENS

<400> SEQUENCE: 3

```
tttatggcat ttaagtcttt tgcagatctt cagcataagc ctctgctcgt tgacctcaca      60
gtagaagaag gtcaaaggtt aaaggtcatt tttggctcac acactggttt ccatgtaatt     120
gatgttgact ctggaaactc ctacgatatc tatataccat cccatattca gggtaatatc     180
actcctcacg ctatcgtcat cttgcctaaa acagacggaa tggagatgct tgtctgctat     240
gaggatgagg gggtgtatgt gaacacctat ggccggatca ctaaggatgt ggtgctccaa     300
tggggagaaa tgcccacatc tgtgggtagg ttaaccattc cttatctcct tcagcagttc     360
cacccccaa atgaaacgaa gggcaagaaa tgtgaaacaa ccatttgagt tcacaaaaaa     420
aaaa                                                                  424
```

<210> SEQ ID NO 4
<211> LENGTH: 135
<212> TYPE: PRT
<213> ORGANISM: HOMO SAPIENS

<400> SEQUENCE: 4

```
Phe Met Ala Phe Lys Ser Phe Ala Asp Leu Gln His Lys Pro Leu Leu
 1               5                  10                  15
Val Asp Leu Thr Val Glu Glu Gly Gln Arg Leu Lys Val Ile Phe Gly
            20                  25                  30
Ser His Thr Gly Phe His Val Ile Asp Val Asp Ser Gly Asn Ser Tyr
        35                  40                  45
Asp Ile Tyr Ile Pro Ser His Ile Gln Gly Asn Ile Thr Pro His Ala
    50                  55                  60
Ile Val Ile Leu Pro Lys Thr Asp Gly Met Glu Met Leu Val Cys Tyr
65                  70                  75                  80
Glu Asp Glu Gly Val Tyr Val Asn Thr Tyr Gly Arg Ile Thr Lys Asp
                85                  90                  95
Val Val Leu Gln Trp Gly Glu Met Pro Thr Ser Val Gly Arg Leu Thr
            100                 105                 110
Ile Pro Tyr Leu Leu Gln Gln Phe His Pro Pro Asn Glu Thr Lys Gly
        115                 120                 125
Lys Lys Cys Glu Thr Thr Ile
    130                 135
```

<210> SEQ ID NO 5
<211> LENGTH: 1402
<212> TYPE: DNA
<213> ORGANISM: HOMO SAPIENS

<400> SEQUENCE: 5

```
gcaagcctgc catagacaca gcaggcacca acaagtcaga ttttagggaa cctgaaggca      60
aggctttgac aaaattctaa gattccaatc atgttatgtt cctccaaact tcccaacata     120
ctgttaacaa catctgtgca gagatgtgta tgtatttagt tcaggttgac ttgtgtcctt     180
atagaaaccc ttactcgaat gatttgaacc tttatgtgac tgactgggat tttcccccaaa    240
gctccaagca tggccgccta tggtatccag gtgttgcaaa atggtatctg tgctgtgctt     300
cctgttttaa cctacctcgt tttgtttgwt tttgtttctc tgttcatcac agcagkgtta     360
tctccaggag acatatatag agctcacccg gcaatctcaa gctgkcttga cattttcaa     420
aacaagtagt tgaccaaatt cttytttaaa aaattggagr ggagaaaata aaatctccaa     480
tgacaagaaa ctaatgcrag ctattttttga aagaaatgca awttactggt aaatggatca     540
```

```
aaaaagaaag acaaaaaccc gtgccthtcc tgawcttkgc ctaaacaaat gagcagctga    600
tgttctatta atgagaacga aacacatgtt aggaaaacgg tacctttta atctggtggt    660 tggccaaagg ggatgagaaa gagaactatt ctgagttctg gactanggtg aatctggtaa    720
tccccaaagg gtgattgkta tttgtagtta tctgaagcag gntaacacac agaaatccag    780
tgagggtggt cttcaagtga tcaccaggat gtgtccatca tggccctct agctctcaaa    840 ggcaatgaaa tcctcccgtt ctcatttta ctgctggggt tatgctgccg aacaacactg    900
tccttacgaa ttccacagga caaattcagc aatagctctg ggttgaattt agcgactaca    960
ataattggat gccgatgcgg acaaaaataa tatggatttg ggtcttgtct ccaaatgtgg   1020
ttgccaccag ctctttatat cactgctgtg atgttttcaa cctgaggctt ctttaaatta   1080
cgttgcaaac tgatctttg tctttatgtt tcgtgccact ttgttcttac ttctaagcgt   1140
acatctgaaa cacacagctt taaatgattt ttttattgtg ggactttggg tacagttaag   1200
aaataaaagg gaatcattgt gtttaaacat aaggtagttt gtgaatgtat ttttaaaat   1260 ctagattcat tggaacaaga aaaccataag aaaacatatt aatgccgtct tgtttacagt   1320
atggacagtg gcataacatt acatgagctt tttctggtgc caacaaaata aaacacagac   1380
gttaaacatc aaaaaaaaaa aa                                           1402
```

KIAA0551 POLYNUCLEOTIDES AND POLYPEPTIDES USE

FIELD OF THE INVENTION

Figure 1B:
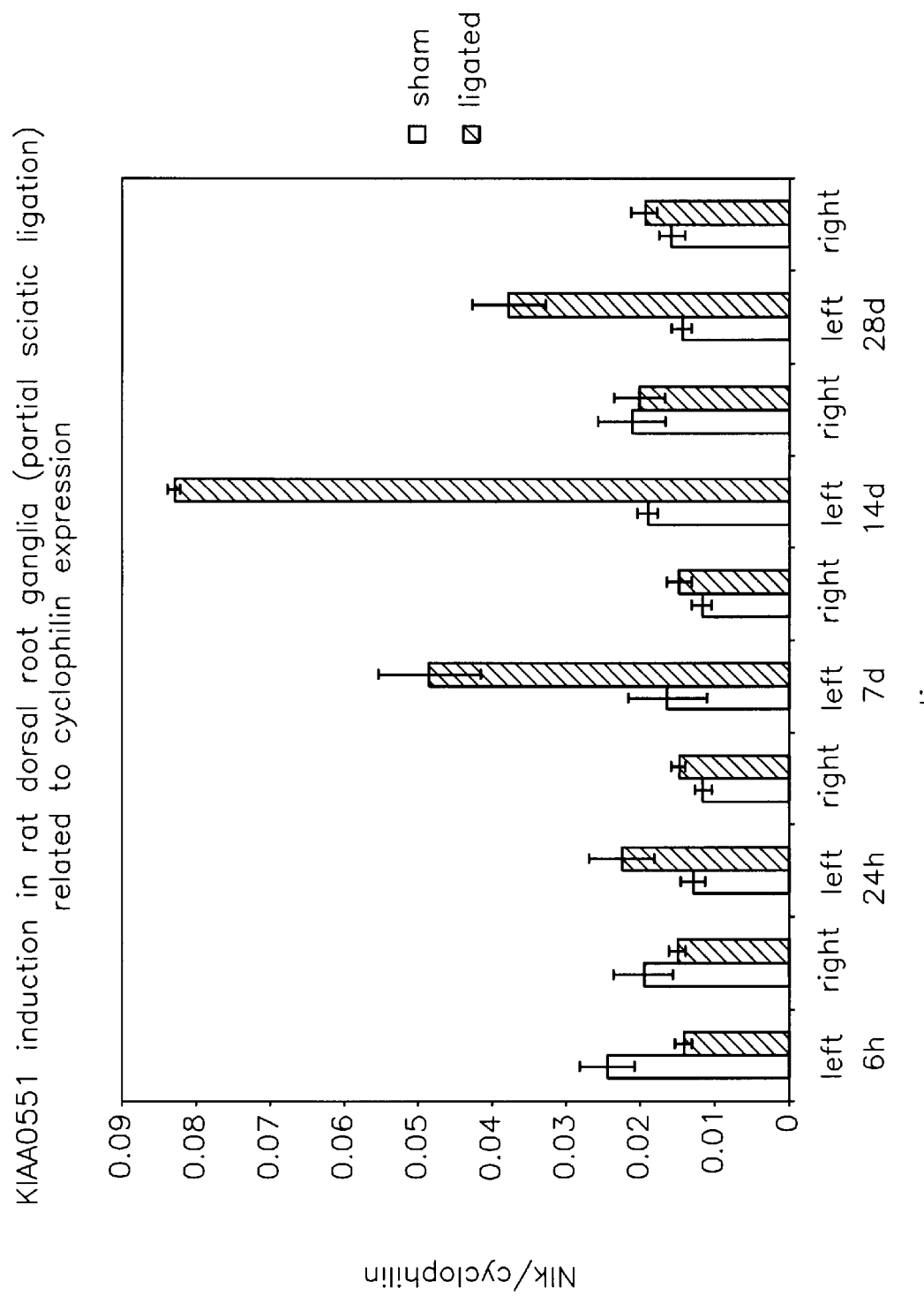

This invention relates to new uses for polynucleotides and polypeptides encoded by them, to their use in therapy and in identifying compounds which may be agonists, antagonists and/or inhibitors which are potentially useful in therapy, to production of such polypeptides and polynucleotides, and to the identification of new full-length polynucleotides and polypeptides.

SUMMARY OF THE INVENTION

In one aspect, the invention relates to new uses of KIAA0551 polynucleotides and polypeptides (Nagase et al., 1998, DNA Res.5, 31–39. Genbank acc. no. AB01123). Such uses include the treatment and/or prophylaxis of neuropathies, neuropathic pain, inflammatory and chronic pain, neurodegenerative conditions such as Motor Neuron Disease, Parkinson's Disease, Alzheimer's Disease and other dementias, as well as neuronal degeneration resulting from ischemic events, including cerebral ischemia after cardiac arrest, stroke and multi-infarct dementia and also after cerebral ischemic events such as those resulting from surgery and/or during childbirth, hereinafter referred to as "the Diseases," amongst others.

Thus according to one aspect of the invention there is provided a method of treatment or prophylaxis of a neurotraumatic disease. Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

In another aspect the invention relates to KIAA0551 recombinant materials and methods for their production. In a further aspect, the invention relates to methods for identifying agonists and antagonists/inhibitors using the materials provided by the invention, and treating conditions associated with KIAA0551 imbalance with the identified compounds. In a still further aspect, the invention relates to diagnostic assays for detecting diseases associated with inappropriate KIAA0551 activity or levels. In a yet further aspect the invention relates to newly identified full-length KIAA0551 polynucleotides and to their use in therapy, diagnosis and methods for identifying antagonists and agonists.

DESCRIPTION OF THE INVENTION

In a first aspect, the present invention relates to the use of a compound selected from:
(a) a KIAA0551 polypeptide;
(b) a compound which activates a KIAA0551 polypeptide; or
(c) a compound which inhibits a KIAA0551 polypeptide; or
(d) a polynucleotide encoding a KIAA0551 polypeptide, for the manufacture of a medicament for treating:
  (i) neuropathies;
  (ii) neuropathic pain;
  (iii) inflammatory and chronic pain;
  (iv) neurodegenerative conditions;
  (v) neurotraumatic disease or ischaemic damage in cardiac tissues.

Such KIAA0551 polypeptides include isolated polypeptides comprising an amino acid sequence which has at least 95% identity, preferably at least 97–99% identity, to that of SEQ ID NO:2 over the entire length of SEQ ID NO:2. Such polypeptides include those comprising the amino acid sequence of SEQ ID NO:2.

Further polypeptides of the present invention include isolated polypeptides in which the amino acid sequence has at least 95% identity, preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO: 1.

Such polypeptides are new and form part of the present invention.

Human KIAA0551 has been described as a partial cDNA sequence isolated from human brain (Nagase et al, 1998, DNA Res. 5, 31–39). This sequence encodes a polypeptide with no assigned function but with some predicted structural similarity to Sterile 20-family of protein kinases, in particular to murine NIK (Su et al., 1997, EMBO J. 16, pp.1279–1290).

Using standard differential display techniques as well as quantitative RT-PCR (TaqMan™) techniques, it has been shown that KIAA0551 mRNA is upregulated in dorsal root ganglia (DRGs) during rat sciatic neuropathy, a procedure accompanied by increased sensitivity to somatic pain (SEQ ID NO:3, SEQ ID NO: 5 and FIGS. 1a and b). The polynuclcotide sequences SEQ ID NO:3 and SEQ ID NO:5 represent the partial rat KIAA0551 cDNA fragrnents isolated in the differential display. The amino acid sequence of SEQ ID NO:4 is the predicted polypeptide sequence encoded by the polynucleotide of SEQ ID NO:3. The full length human KIAA0551 cDNA has been cloned from a human foetal brain cDNA library using standard PCR and RACE-PCR techniques (Ausubel et al. (Ed.), Current Protocols in Molecular Biology, Vol. 2, John Wiley & Sons, (1996)). The polynucleotide sequence SEQ ID NO:1 represents full length human KIAA0551 cDNA. The amino acid sequence of SEQ ID NO:2 is the predicted polypeptide sequence encoded by the polynucleotide of SEQ ID NO:1. The full length KIAA0551 cDNA encodes 27 additional amino acids N-terminal to the published sequence which completes the kinase domain. Analysis of the full-length protein reveals a putative kinase domain (amino acid residues 25–289), two NIK-like domains (amino acid residues 290–506, 668–845) and a CNH domain (amino acid residues 1059–1309) of unidentified function. Using a 'Prosite' motif search, putative tyrosine phosphorylation sites at tyrosine residues 321, 323 and 446, putative cAMP/cGMP-dependent phosphorylation sites at serine residues 77, 259, 688, 915 and 1021 and threonine residues 87 and 827, as well as putative protein kinase C dependent phosphorylation sites at serine residues 255, 275, 528, 630, 755, 795, 968, 1104 and 1348 and threonine residues 124, 309, 349, and 819 have been identified.

Figure 3:
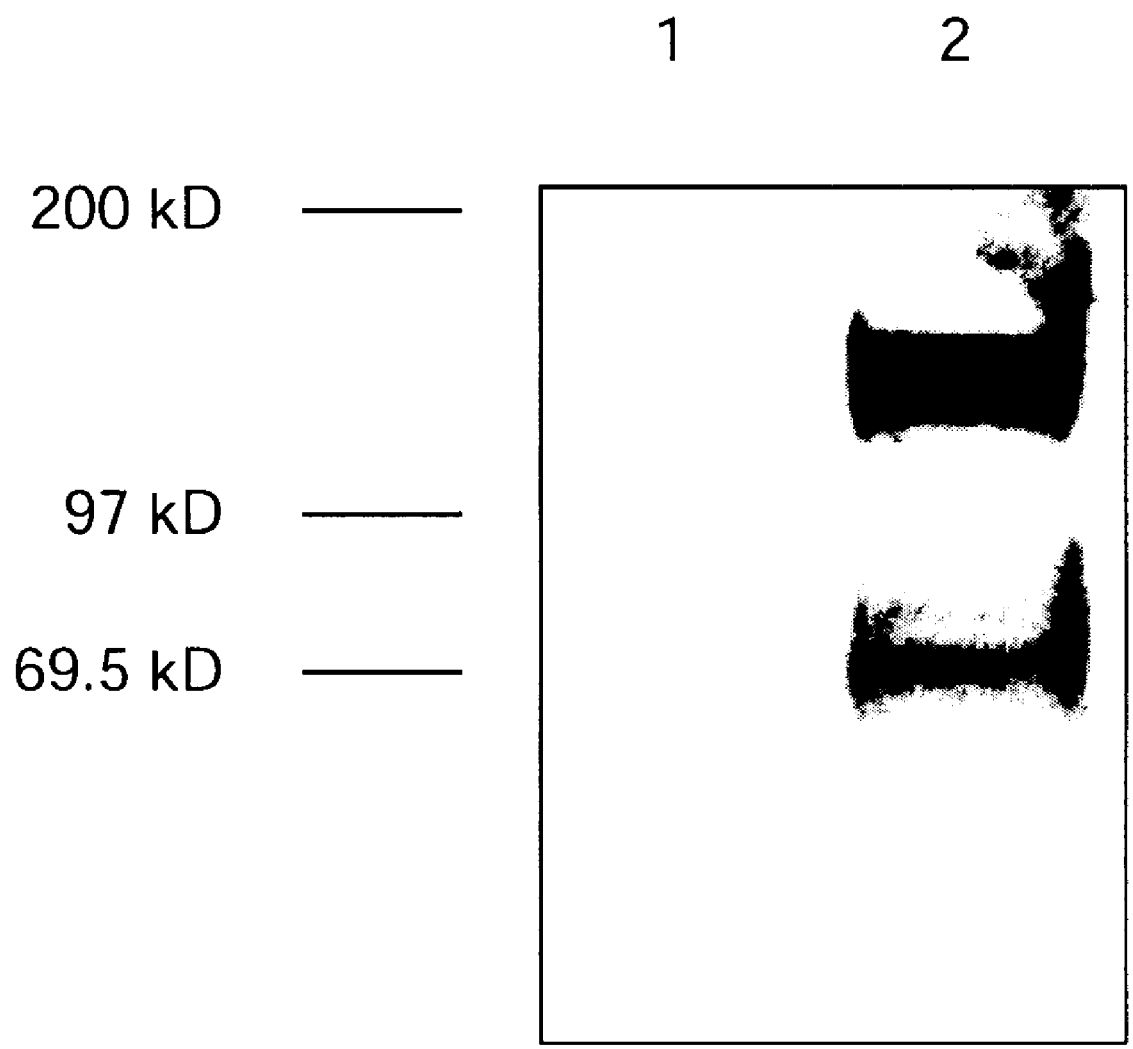
Figure 4:
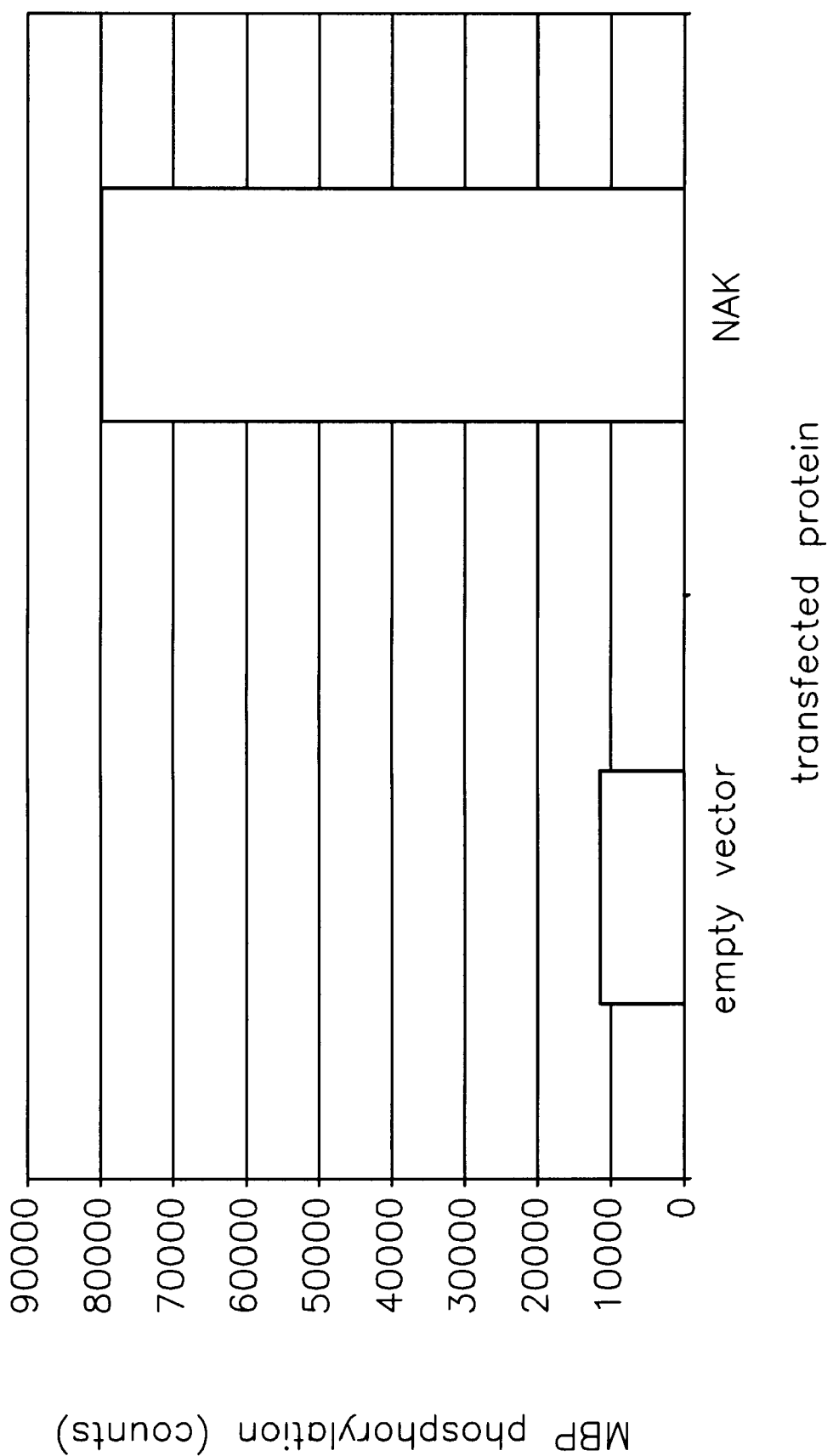
Figure 5:
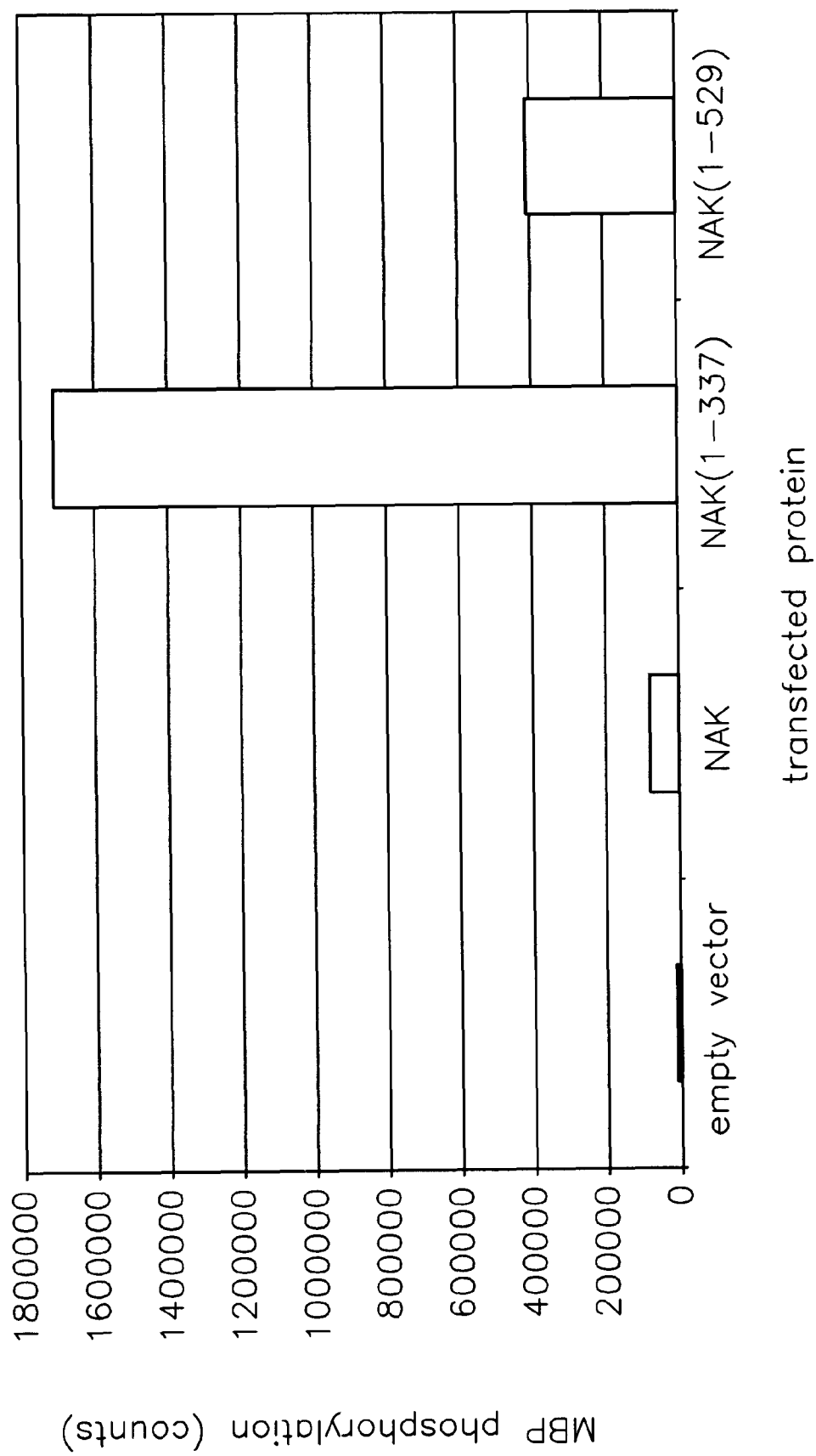

Recombinant human NAK protein has been expressed in HEK293 cells and has been shown, upon isolation, to be protein of 190 kDa (FIG. 3). Recombinant NAK protein displays enzymatic (kinase) activity, demonstrated by the ability of recombinant NAK protein to phosphorylate myelin basic protein (MBP) (FIG. 4a). Furthermore, two C terminal truncates encoding amino acid residues 1–337 (NAK1–337)

or 1–529 (NAK 1–529) display increased kinase activity (FIG. 4b), defining a core catalytic region and suggesting an inhibitory role of the C-terminus of the protein and a putative mode of posttranslational enzymatic regulation.

Polypeptides of the present invention are believed to be members of the Sterile 20 (Ste20)-like protein kinase family of polypeptides (Fanger et al., 1997, Curr. Op. Genet. Dev. 7, 67–74), and show most homology to murine NIK (Su et al., 1997, FMBO J. 16, pp.1279–1290). They are therefore of interest because:

i) such proteins have been shown to act as activators of the Stress-activated protein kinase (SAPK) pathways, which have been implicated in the regulation of apoptotic cell death in neuronal cells and tissues (Fanger et al., 1997, Curr. Op. Genet. Dev. 7, 67–74);

ii) such proteins have been shown to act as activators of the NF-κB pathway, which has been implicated in inflammation control (Malinin et al, Nature 385, pp. 540–544 (1997); Mercurio and Manning, Curr. Op. Cell Biol. 11, pp. 226–232 (1999); Bacuerle, Cell 95, pp.729–731 (1998); Yin et al., Nature 396, pp.77–80 (1998));

iii) KIAA0551 mRNA is expressed broadly in human CNS (FIG. 2); and iv) the mRNA of the rat ortholog of KIAA0551 is upregulated during rat sciatic neuropathy, a procedure accompanied by increased sensitivity to somatic pain (SEQ ID NO:3, SEQ ID NO: 5 and FIGS. 1a and b).

These properties are hereinafter referred to as "KIAA0551 activity" or "KIAA0551 polypeptide activity" or "biological activity of KIAA055 1". Also included amongst these activities are antigenic and immunogenic activities of said KIAA0551 polypeptides, in particular the antigenic and immunogenic activities of the polypeptide of SEQ ID NO:2. Preferably, a polypeptide of the present invention exhibits at least one biological activity of KIAA0551.

The polypeptides of the present invention may be in the form of the "mature" protein or may be a part of a larger protein such as a precursor or a fusion protein. It is often advantageous to include an additional amino acid sequence which contains secretory or loader sequences, prosequences, sequences which aid in purification such as multiple histidine residues, or an additional sequence for stability during recombinant production.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to KIAA0551 polynucleotides. Such polynucleotides include isolated polynucleotides comprising a nucleotide sequence encoding a polypeptide which has at least 95% identity to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 95% identity to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 95% identity to SEQ ID NO:1 over the entire length of SEQ ID NO:1. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides. Such polynucleotides are new and form part of the present invention.

The nucleotide sequence of SEQ ID NO:1 shows homology with the Sterile 20 family of protein kinases, of which it is most similar to murine NIK (Su et al., 1997, EMBO J. 16, 1279–1290. Genbank acc. no. U88984) The nucleotide sequence of SEQ ID NO:1 is a CDNA sequence and comprises a polypeptide encoding sequence (nucleotide 99 to 4178) encoding a polypeptide of 1360 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the Ste20-family of protein kinases, having homology and/or structural similarity with murine NIK (Su et al., 1997, FMBO J. 16, 1279–1290. Genbank acc. no. U88984).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one KIAA0551 activity.

Polynucleotides of the present invention may be obtained, using standard cloning and screening techniques, from a cDNA library derived from mRNA in cells of human foetal brain (Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted deleted or added, in any combination.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptoinyces and *Bacillus subtilis* cells; fungal cells, such as yeast cells and Aspergillus cells; insect cells such as Drosophila S2 and Spodoptera Sf9 cells; animal cells such as CHO, COS, Hel,a, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characterised by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled KIAA0551 nucleotide sequences. Perfectly matched sequences can be distinguished from mismatched duplexes by Rnase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science (1985) 230:1242). Sequence changes at specific locations may also be revealed by nuclease protection assays, such as Rnase and S1 protection or the chemical cleavage method (see Cotton et al., Proc Natl Acad Sci USA (1985) 85: 4397–4401). In another embodiment, an array of oligonucleotides probes comprising KIAA0551 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M.Chee et al., Science, Vol 274, pp 610–613 (1996)).

The diagnostic assays offer a process for diagnosing or determining a susceptibility to the Diseases through detection of mutation in the KIAA0551 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, Rnase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:
(a) a polynucleotide of the present invention, preferably the nucleotide sequence of SEQ ID NO: 1, or a fragment thereof;
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or suspectability to a disease, particularly neuropathies, neuropathic pain, inflammatory and chronic pain, neurodegenerative conditions such as Motor Neuron Disease, Parkinson's Disease, Alzheimer's Disease and other dementias, as well as ischaemic damage in neuronal and cardiac tissues, amongst others.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fe part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for one or more biological functions, including one or more disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring KIAA0551 activity in the mixture, and comparing the KIAA0551 activity of the mixture to a standard. Fusion proteins, such as those made from Fe portion and KIAA0551 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify interacting proteins or other molecules. For example the identification of interacting kinases may help to elucidate the signalling pathway of which KIAA0551 forms a part. These methods include, but are not limited to, two-hybrid system (Fields and Song, Nature 340, pp. 245–246 (1989); Durfee et al., Genes Dev. 7, pp. 555–569 (1993); Bartel and Fields, Methods in Enzymology 254, pp. 241–262 (1995)), λgt11 expression cloning (Blackwood and Eisenmann, Methods in Enzymology 254, pp. 229–240 (1995)), expression screening for protein kinase substrates (Fukunaga and Hunter, EMBO J. 16, pp. 1921–1933 (1997)) as well as coimmunoprecipitation and western blotting assays (Ransone, Methods in Enzymology 254, pp. 491–496 (1995), Okamura et al., Methods in Enzymology 254, pp. 535– 549 (1995)). These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypetide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention; which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesing candidate compounds that are predicted to bind to or react with the deduced binding or reactive site; and (d) testing whether the candidate compounds are indeed agonists, antagonists or inhibitors.

It will be further appreciated that this will normally be an interative process.

In a further aspect, the present invention provides methods of treating abnormal conditions such as, for instance, neuropathies, neuropathic pain, inflammatory and chronic pain, neurodegenerative conditions such as Motor Neuron Disease, Parkinson's Disease, Alzheimer's Disease and other dementias, as well as ischaemic damage in neuronal and cardiac tissues, related to either an excess of, or an under-expression of, KIAA0551 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the KIAA0551 polypeptide.

In still another approach, expression of the gene encoding endogenous KIAA0551 polypeptide can be inhibited using expression blocking techniques. Known such techniques involve the use of antisense sequences, either internally generated or externally administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administeredperse or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human KIAA0551 polypeptide may be prevented by using ribozymes specific to the human KIAA0551 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave human KIAA0551 mRNAs at selected positions thereby preventing translation of the human KIAA0551 mRNAs into functional polypeptide. Ribozymes may be synthesised with a natural ribose phosphate backbone and natural bases, as normally found in RNA molecules. Alternatively the ribozymes may be synthesised with non-natural backbones to provide protection from ribonuclease degradation, for example, 2'-O-methyl RNA, and may contain modified bases.

For treating abnormal conditions related to an underexpression of KIAA0551 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of KIAA0551 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Geneticbased Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as those in the GCG or Lasergene software packages. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. "Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, pgs. 1–12 in Post-translational Covalent Modification of Proteins, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:48–62).

"Full-length" refers to both isolated polynucleotide and polypeptide sequences. Within the meaning of the term as used herein, a polypeptide is full-length when it has the complete translated amino acid sequence of a naturally occuring polypeptide, prior to any subsequent processing, for example signal peptide cleavage, or conversion to an active form facilitated by protease cleavage of a precursor polypeptide form. The amino acid sequence of the natural full-length polypeptide can be predicted from the coding sequence of the DNA or RNA polynucleotides which encodes it according to the established genetic code of the source organism or, if it is to be expressed in a host cell of a different species, the actual expressed polypeptide sequence will be determined by the genetic code of the host. Such methods of prediction are well known in the art, and include translation software such as that in the Lasergene or GCG DNA and protein analysis software packages. It will be appreciated by one skilled in the art that once the full-length polypeptide has been expressed in a host cell, it may be subject to further protease mediated processing, such as removal of a signal peptide, or cleavage to an active form. Full-length polypeptides include all those arising from differential splicing of the primary mRNA transcript. Full-length polypeptides encoded by the same genomic sequence may therefore be of different lengths according to which exons, if any, have been excised from the primary mRNA during splicing. Such splicing and the consequences of this in terms of polypeptide length are well known to those skilled in the art.

A polynucleotide is full-length if it has the full coding capacity to enable the production of a full-length polypeptide according to the definition hereinabove given when the polynucleotide is introduced into a suitable environment for expression, for example when inserted into an expression vector and present in a compatible host. Full-length polynucleotides include those that arise as a result of differential splicing from the primary mRNA transcript. Thus full-length polynucleotides include those comprising all exons, or those where one or more exons have been removed by splicing.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., el al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%,etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species, and "paralog" meaning a functionally similar sequence when considered within the same species.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication

EXAMPLES

Example 1

Application of Differential Display to Neuropathic Pain

The Differential Display Technique

This PCR-based technique (Liang P, Pardee A B., Science 1992; 257:967–971) has several advantages over the previous methods for isolating differentially expressed genes including:

(I) The ability to simultaneously analyze multiple samples, (II) The simultaneous detection of decreased and increased expression, (III) High sensitivity which allows detection of low-copy number mRNAs, (IV) Low quantity of mRNA required, (V) Ability to detect mRNAs encoding novel members of gene families that are easily lost as double-stranded molecules during subtractive hybridization, (VI) Fast procedure with band patterns obtained in two days and clones in four days.

The general experimental approach is based on the generation of sub-populations of RT-PCR products on a polyacrylamide gel. Two distinct PCR primers are utilized:

1) An anchored 3' oligo-(dT) primer $dT_{12}$(G/C/A)(G/C/A/T), with one of the twelve possibilities, $dT_{12}$GG. Each primer therefore selects for approximately 1/12th of the mRNA. Since ~15,000 different species of mRNA are present in a given cell then a sub-set of approximately 1,250 cDNAs is generated by each anchored primer. 2) A 5' arbitrary primer of defined sequence which, at an appropriate annealing temperature, will hybridize to a proportion of each cDNA sub-set at a region of varying distances from their 3' end. 50–100 bands of different cDNA sizes will be generated for a given arbitrary and anchored primer combination following PCR amplification.

Inclusion of a radiolabeled nucleotide in the PCR reaction mixture allows the products to be visualized by autoradiography following denaturing polyacrylamide gel electrophoresis. The use of different arbitrary 5' primers in combination with each of the twelve 3' primers should lead to the display of the majority of transcripts present in a cell. Differential expression is assessed by visual comparison of the banding pattern across lanes. The vast majority of PCR products will be identical between samples, with the occasional band differences representing a putative differentially expressed mRNA. The gel region containing the differential band is excised, the DNA eluted and reamplified using the original primer combination and then finally cloned into a plasmid vector. The clones are used to confirm differential expression, either by using them directly as probes against Northern blots or by designing specific oligonucleotides for use in RT-PCR or in situ hybridization experiments.

Experimental Design

Differential display has previously been successfully utilized to identify genes expressed in regenerating motor and sensory neurons following crush injury of the sciatic nerve (Livesey F J, O'Brien J A, Li M, Smith A G, Murphy L J, Hunt S P., Nature 1997; 390:614–618). We wanted to identify genes associated with painful neuropathy, particularly with regard to diabetic neuropathy, one of the major complications of diabetes. We therefore used an animal model of neuropathic pain based on a unilateral partial injury of the sciatic nerve (Seltzer Z, Dubner R, Shir Y., Pain 1990, 43:205–218) and applied it to Zucker Diabetic Fatty (ZDF) rats in addition to lean (LN) non-diabetic rats. Differential display was then used to assess changes in gene expression in ipsilateral and contralateral $L_4$ and $L_5$ DRG. The presence of diabetes may augment/depress expression of injury-related genes and change expression of novel genes. A similar experimental design was used to examine expression of growth-associated proteins following crush injury in control and streptozotocin-induced diabetic rats (Mohiuddin L, Tomlinson, DR., Diabetes 1997; 46:2057–2062).

Approximately half the sciatic nerve was unilaterally ligated high in the thigh of LN and hyperglycaemic ZDF rats. Thermal hyperalgesia was assessed as a withdrawal latency from a nociceptive temperature applied separately to each foot. 14 days post-surgery, thermal hyperalgesia was tested and animals only used for differential display if they showed both guarding of the ipsilateral paw and a ratio of latency at day 14/pre-surgery baseline latency for the ipsilateral side that was <0.8. $L_4$ and $L_5$ DRG were isolated from the ipsilateral (L) and contralateral (R) side of hyperalgesic and sham-operated rats and total RNA prepared. DRG from several hyperalgesic animals were also retained for in situ experiments. Differential display analysis was performed using the Hieroglyph mRNA Profile System (Genomyx Corporation).

Probably the major disadvantage reported with differential display is a potentially high false positive rate where clones isolated from differential bands on a gel subsequently fail to replicate the expression pattern in confirmation experiments. Therefore we incorporated several strategies to diminish this possibility:

(I) RNA isolations were processed as a batch to increase standardization between animals then aliquots of RNA pooled as detailed below.

(II) For both ZDF and LN hyperalgesic rats, the animals were divided into two pools (A and B) which both had similar mean levels of hyperalgesia. This gave eight RNA sample lanes:

| POOL A | | POOL B | | POOL A | | POOL B | |
|---|---|---|---|---|---|---|---|
| ZDF | ZDF | ZDF | ZDF | LN | LN | LN | LN |
| (L) | (R) | (L) | (R) | (L) | (R) | (L) | (R) |

Only changes that were replicated between the independent pools were considered for further analysis.

(III) Sham ZDF and sham LN controls were included to give a further four lanes:

| Sham ZDF | Sham ZDF | Sham LN | Sham LN |
|---|---|---|---|
| (L) | (R) | (L) | (R) |

(IV) Extended sequencing gels were run on the GenomyxLR DNA sequencer to maximize resolution of bands and hence avoid cloning similarly migrating sequences.

(V) Long anchor and arbitrary primers were used. Following low stringency annealing for the first few cycles of PCR, these could be used under stringent conditions for subsequent cycles thereby preventing mispriming during the amplification process.

(VI) RNA samples where no reverse transcriptase was added were also used as a template to check for the presence of DNA contamination from the RNA isolation procedure.

Technique

We utilized 22 different arbitrary primers which can be used in combination with the 12 anchored primers to give a possible 264 primer combinations. Since 50–100 bands are observed per gel, this number of combinations would display around 20,000 mRNAs, the approximate number in a cell. However this does not take into account the inevitable redundancy of the displays, i.e., some mRNAs will be displayed more than once while others, particularly rare messages, will not be detected. Despite incomplete coverage of the mRNA population with such primer combinations, the technique still provides an excellent chance of detecting important changes in gene expression under conditions where the number of genes differentially expressed is fairly high.

A majority of clones isolated fail to match known genes. This could be due to the mRNA identified being novel or it may be a consequence of the 3' UTR targeting inherent with differential display and therefore represent the 3' UTR of a characterised mRNA whose sequence in this region is unknown. This latter possibility is reduced in our system by the bands selected being between 0.4 and 1.8 Kb which increases the chance of obtaining sequence information in the coding region. The 5' upstream sequence of the confirmed differential clones that appear novel are being determined using the 5' RACE method.

The results demonstrate the ability of the technique to identify differentially expressed genes in a pain model when the appropriate experimental strategies are adopted.

The polynucleotide sequences SEQ ID NO:3 and SEQ ID NO:5 are the sequences of two of the bands isolated by the hereinabove described differential display experiment. The amino acid sequence of SEQ ID NO:4 is the predicted polypeptide sequence encoded by the polynucleotide of SEQ ID NO:3.

Conclusions

The polynucleotide sequences SEQ ID NO:3 and SEQ ID NO:5 identify KIAA0551 as a gene differentially expressed in $L_4$ and $L_5$ DRG in a rat model of neuropathic pain. This finding strongly indicates a role for KIAA0551 in the regulation of molecular processes associated with neuropathy and neuropathic pain that might be involved in the development of hyperalgesia and neurodegeneration.

Example 2

Application of Quantitative RT-PCR (TaqMan™) to Neuropathic Pain

Changes in KIAA0551 gene expression in ipsilateral and contralateral $L_4$ and $L_5$ DRG of lean (LN) non-diabetic rats in response to a unilateral partial injury of the sciatic nerve as described above (Seltzer Z, Dubner R, Shir Y., Pain 1990, 43:205–218) were also determined using TaqMan™ quantitative PCR. TaqMan™ is a known quantitative PCR-technique for determination of starting concentrations of template, based on the 5'-3' exonuclease activity of *Thermus aquaticus* (Taq) polymerase as described in Lie and Petropoulos, Curr. Op. Biotechnolgy 9, pp. 43–48 (1998). RNA was prepared from $L_4$ and $L_5$ DRG following standard procedures and reverse transcribed in vitro (Sambrook et al., Molecular Cloning: A Laboratory Manual, 2nd Ed., Cold Spring Harbor Laboratory Press, Cold Spring Harbor, N.Y. (1989)). cDNA from this reaction was then subjected to TaqMan™ analysis using a ABI PRISMTM 7700 Sequence Detector following standard manufacturers instructions (PerkinElmer Applied Biosystems). Each data point represents triplicate values from a pool of reverse transcribed RNA from three hyperalgesic or sham operated control rats.

The expression profile of KIAA0551 mRNA in human CNS and peripheral tissues was determined by TaqMan™ analysis of reverse transcribed human RNA (Clontech) as described above.

Conclusions

These data validate the findings from the initial differential display and confirm KIAA0551 as a gene upregulated in $L_4$ and $L_5$ DRG during neuropathic pain. In addition they show that KIAA0551 mRNA expression in $L_4$ and $L_5$ DRG is permanently upregulated between 7–28 days post sciatic ligation, further suggesting that this gene is involved in regulation of the molecular processes and signalling pathways that are active during neuropathic pain. The potential role of KIAA0551 in neuropathies further suggests a general role for KIAA0551 in the regulation of neurodegenerative processes, particularly since the identification of KIAA0551 as a gene expressed in human CNS implies further roles for this gene in the regulation of neuronal processes.

Example 3

Cloning of Full-length Human KIAA0551

A human foetal brain cDNA library was constructed from reverse transcribed human foetal brain RNA (Clontech). This library was used as a template to amplify the published partial KIAA0551 sequence (Nagase et al., 1998, DNA Res.5, 31–39. Genbank acc. no. AB011123) using specific primer sets for the coding sequence. The polynucleotide sequence of the 5'-end was isolated by RACE-PCR following standard procedures (Ausubel et al. (Ed.), Current Protocols in Molecular Biology, Vol. 2, John Wiley & Sons, (1996)), and was used to generate a full-length KIAA0551 construct. The full-length polynucleotide sequence is given in SEQ ID NO:1 and the encoded polypeptide in SEQ ID NO:2.

Example 4

Expression of Recombinant NAK Protein in HEK293 Cells and Demonstration of Kinase Activity Against Myelin Basic Protein (MBP)

A mammalian NAK recombinant expression construct containing hexa His and myc epitope tags (pcDNA3.1.NAK-Hm) was generated by cloning full-length human NAK cDNA into the mammalian expression vector pcDNA3.1-His-myc (Invitrogen) following standard procedures (Sambrook et al.,full reference page 5 line 31). In addition, two 5'-terminally truncated human NAK cDNAs encoding His and myc epitope tagged NAK amino acids 1–337 and 1–529, respectively, were generated by PCR (Ausubel et al. (Ed.), Current Protocols in Molecular Biology, Vol. 2, John Wiley & Sons, (1996)) and cloned into pcDNA3.1-His-myc to give pcDNA3.1.NAK(1–337)-Hm and pcDNA3.1.NAK(1–529)-Hm.

4$\mu$g of pcDNA3.1-His-myc, pcDNA3.1.NAK-Hm, pcDNA3.1.NAK(1–337)-Hm or pcDNA3.1.NAK(1–529)-Hm were transfected into $3 \times 10^6$ HEK293 cells on 10 cm tissue culture dishes using LipofectAmine Plus™ (Life Technologies) reagent following manufacturer's instructions. 48 h post transfection cells were washed once in ice-cold phosphate-buffered saline and lysed in 1 ml ice-cold lysis buffer (20 mM HEPES pH8.0, 50mM NaF, 25 mM NaCl, 20 mM β-glycerophosphate, 2 mM EDTA, 1 mM Na-vanadate, 0.5 mM DTT, supplemented with Complete™ (Boehringer Mannheim) protease inhibitor) for 10 minutes at 4° C. Lysates were cleared of debris by centrifugation for 10 minutes at 14000 rpm at 4° C. Total protein concentration of cleared lysates was determined by protein assay following standard procedures (Ausubel et al. (Ed.), supra) and lysates were stored at −80° C. until further analysis.

Lysates were analysed for NAK protein expression by discontinuous SDS-polyacrylamide gel electrophoresis. Gels were transferred to nitrocellulose and NAK protein was visualized by immunoblotting using anti-myc antibody 9E10 (SantaCruz) following standard procedures (Ausubel et al. (Ed.), supra).

Expression levels of full-length and truncated recombinant human NAK proteins in transfected HEK293 cells were comparable. Enzymatic activity of HEK293-derived NAK proteins was determined following immunoprecipitation of NAK proteins from lysates containing 500 μkg total protein using 2 μg anti-myc (9E10) antibody (SantaCruz) following standard procedures (Ausubel et al. (Ed.), supra). Immunoprecipitates were washed three times in ice-cold lysis buffer and once in ice-cold kinase buffer (20 mM HEPES pH7.4, 20 mM β-glycerophosphate, 10 mM NaF, 10 mM $MgCl_2$, 1 mM DTT, 200 μM Na-vanadate). Kinase activity was determined by incubation of immunoprecipitates in 30 μl kinase assay buffer (20mM HEPES pH7.4, 20 mM β-glycerophosphate, 10 mM NaF, 10 mM $MgCl_2$, 1 mM DTT, 200 μM Na-vanadate, 10 μM ATP, 250 μg/ml myelin basic protein (MBP) (Sigma) and 165 μCi/ml γ-32P-ATP (specific activity 5000 Ci/mmol; Amersham)) for 30 minutes at 30° C. MBP was bound to P81 chromatography paper by spotting 15 μl of each reaction on pre-cut P81 paper squares which were washed 5×2 min in 75 mM orthophosphoric acid. Incorporation of phosphate in MBP was determined by counting P81 paper squares with 4 ml of UltimaGold™ XR scintillation fluid (Packard) in a 2500TR scintillation counter (Packard).

Conclusions

These data confirm NAK as an enzymatically active protein kinase. The finding that deletion of the C-terminus increases kinase activity defines a core catalytic region within aa1–337 and further suggests an inhibitory role of the C-terminus and the presence of a C-terminal negative regulatory domain.

SEQUENCE INFORMATION

SEQ ID NO:1

CACCCGCATGAGGACGCGAGTGAAATAGACCAAGGTGGAATTTCCAAGGG

AAAAGCTTCGGGGTGGTTTTGGTCCATTTCTCCAGCGAAGAAGTAGACAT

GGCGAGCGACTCCCCGGCTCGAAGCCTGGATGAAATAGATCTCTCGGCTC

TGAGGGACCCTGCAGGGATCTTTGAATTGGTGGAACTTGTTGGAAATGGA

ACATACGGGCAAGTTTATAAGGGTCGTCATGTCAAAACGGGCCAGCTTGC

AGCCATCAAGGTTATGGATGTCACAGGGGATGAAGAGGAAGAAATCAAAC

AAGAAATTAACATGTTGAAGAAATATTCTCATCACCGGAATATTGCTACA

TACTATGGTGCTTTTATCAAAAAGAACCCACCAGGCATGGATGACCAACT

TTGGTTGGTGATGGAGTTTTGTGGTGCTGGCTCTGTCACCGACCTGATCA

AGAACACAAAAGGTAACACGTTGAAAGAGGAGTGGATTGCATACATCTGC

-continued

AGGGAAATCTTACGGGGGCTGAGTCACCTGCACCAGCATAAAGTGATTCA

TCGAGATATTAAAGGGCAAAATGTCTTGCTGACTGAAAATGCAGAAGTTA

AACTAGTGGACTTTGGAGTCAGTGCTCAGCTTGATCGAACAGTGGGCAGG

AGGAATACTTTCATTGGAACTCCCTACTGGATGGCACCAGAAGTTCTTGC

CTGTGATGAAAACCCAGATGCCACATATGATTTCAAGAGTGACTTGTGGT

CTTTGGGTATCACCGCCATTGAAATGGCAGAAGGTGCTCCCCCTCTCTGT

GACATGCACCCCATGAGAGCTCTCTTCCTCATCCCCCGGAATCCAGCGCC

TCGGCTGAAGTCTAAGAAGTGGTCAAAAAAATTCCAGTCATTTATTGAGA

GCTGCTTGGTAAAGAATCACAGCCAGCGACCAGCAACAGAACAATTGATG

AAGCATCCATTTATACGAGACCAACCTAATGAGCGACAGGTCCGCATTCA

ACTCAAGGACCATATTGATAGAACAAAGAAGAAGCGAGGAGAAAAAGATG

AGACAGAGTATGAGTACAGTGGAAGTGAGGAAGAAGAGGAGGAGAATGAC

TCAGGAGAGCCCAGCTCCATCCTGAATCTGCCAGGGGAGTCGACGCTGCG

GAGGGACTTTCTGAGGCTGCAGCTGGCCAACAAGGAGCGTTCTGAGGCCC

TACGGAGGCAGCAGCTGGAGCAGCAGCAGCGGGAGAATGAGGAGCACAAG

CGGCAGCTGCTGGCCGAGCGTCAGAAGCGCATCGAGGAGCAGAAAGAGCA

GAGGCGGCGGCTGGAGGAGCAACAAAGGCGAGAGAAGGAGCTGCGGAAGC

AGCAGGAGAGGGAGCAGCGCCGGCACTATGAGGAGCAGATGCGCCGGGAG

GAGGAGAGGAGGCGTGCGGAGCATGAACAGGAATACATCAGGCGACAGTT

AGAGGAGGAGCAGAGACAGTTAGAGATCTTGCAGCAGCAGCTACTGCATG

AACAAGCTCTACTTCTGGAATATAAGCGCAAACAATTGGAAGAACAGAGA

CAAGCAGAAAGACTGCAGAGGCAGCTAAAGCAAGAAAGAGACTACTTAGT

TTCCCTTCAGCATCAGCGGCAGGAGCAGAGGCCTGTGGAGAAGAAGCCAC

TGTACCATTACAAAGAAGGAATGAGTCCTAGTGAGAAGCCAGCATGGGCC

AAGGAGGTAGAAGAACGGTCAAGGCTCAACCGGCAAAGTTCCCCTGCCAT

GCCTCACAAGGTTGCCAACAGGATATCTGACCCCAACCTGCCCCCAAGGT

CGGAGTCCTTCAGCATTAGTGGAGTTCAGCCTGCTCGAACACCCCCCATG

CTCAGACCAGTCGATCCCCAGATCCCACATCTGGTAGCTGTAAAATCCCA

GGGACCTGCCTTGACCGCCTCCCAGTCAGTGCACGAGCAGCCCACAAAGG

GCCTCTCTGGGTTTCAGGAGGCTCTGAACGTGACCTCCCACCGCGTGGAG

ATGCCACGCCAGAACTCAGATCCCACCTCGGAAAATCCTCCTCTCCCCAC

TCGCATTGAAAAGTTTGACCGAAGCTCTTGGTTACGACAGGAAGAAGACA

TTCCACCAAAGGTGCCTCAAAGAACAACTTCTATATCCCCAGCATTAGCC

AGAAAGAATTCTCCTGGGAATGGTAGTGCTCTGGGACCCAGACTAGGATC

TCAACCCATCAGAGCAAGCAACCCTGATCTCCGGAGAACTGAGCCCATCT

TGGAGAGCCCCTTGCAGAGGACCAGCAGTGGCAGTTCCTCCAGCTCCAGC

ACCCCTAGCTCCCAGCCCAGCTCCCAAGGAGGCTCCCAGCCTGGATCACA

AGCAGGATCCAGTGAACGCACCAGAGTTCGAGCCAACAGTAAGTCAGAAG

GATCACCTGTGCTTCCCCATGAGCCTGCCAAGGTGAAACCAGAAGAATCC

AGGGACATTACCCGGCCCAGTCGACCAGCTAGCTACAAAAAAGCTATAGA

-continued

```
TGAGGATCTGACGGCATTAGCCAAAGAACTAAGAGAACTCCGGATTGAAG
AAACAAACCGCCCAATGAAGAAGGTGACTGATTACTCCTCCTCCAGTGAG
GAGTCAGAAAGTAGCGAGGAAGAGGAGGAAGATGGAGAGAGCGAGACCCA
TGATGGGACAGTGGCTGTCAGCGACATACCCAGACTGATACCAACAGGAG
CTCCAGGCAGCAACGAGCAGTACAATGTGGGAATGGTGGGGACGCATGGG
CTGGAGACCTCTCATGCGGACAGTTTCAGCGGCAGTATTTCAAGAGAAGG
AACCTTGATGATTAGAGAGACGTCTGGAGAGAAGAAGCGATCTGGCCACA
GTGACAGCAATGGCTTTGCTGGCCACATCAACCTCCCTGACCTGGTGCAG
CAGAGCCATTCTCCAGCTGGAACCCCGACTGAGGGACTGGGGCGCGTCTC
AACCCATTCCCAGGAGATGGACTCTGGGACTGAATATGGCATGGGGAGCA
GCACCAAAGCCTCCTTCACCCCCTTTGTGGACCCCAGAGTATACCAGACG
TCTCCCACTGATGAAGATGAAGAGGATGAGGAATCATCAGCCGCAGCTCT
GTTTACTAGCGAACTTCTTAGGCAAGAACAGGCCAAACTCAATGAAGCAA
GAAAGATTTCGGTGGTAAATGTAAACCCAACCAACATTCGGCCTCATAGC
GACACACCAGAAATCAGAAAATACAAGAAACGATTCAACTCAGAAATACT
TTGTGCAGCTCTGTGGGGTGTAAACCTTCTGGTGGGGACTGAAAATGGCC
TGATGCTTTTGGACCGAAGTGGGCAAGGCAAAGTCTATAATCTGATCAAC
CGGAGGCGATTTCAGCAGATGGATGTGCTAGAGGGACTGAATGTCCTTGT
GACAATTTCAGGAAGAAGAATAAGCTACGAGTTTACTATCTTTCATGGT
TAAGAAACAGAATACTACATAATGACCCAGAAGTAGAAAAGAAACAAGGC
TGGATCACTGTTGGGGACTTGGAAGGCTGTATACATTATAAAGTTGTTAA
ATATGAAAGGATCAAATTTTTGGTGATTGCCTTAAAGAATGCTGTGGAAA
TATATGCTTGGGCTCCTAAACCGTATCATAAATTCATGGCATTTAAGTCT
TTTGCAGATCTCCAGCACAAGCCTCTGCTAGTTGATCTCACGGTAGAAGA
AGGTCAAAGATTAAAGGTTATTTTTGGTTCACACACTGGTTTCCATGTAA
TTGATGTTGATTCAGGAAACTCTTATGATATCTACATACCATCTCATATT
CAGGGCAATATCACTCCTCATGCTATTGTCATCTTGCCTAAAACAGATGG
AATGGAAATGCTTGTTTGCTATGAGGATGAGGGGGTGTATGTAAACACCT
ATGGCCGGATAACTAAGGATGTGGTGCTCCAATGGGGAGAAATGCCCACG
TCTGTGGCCTACATTCATTCCAATCAGATAATGGGCTGGGGCGAGAAAGC
TATTGAGATCCGGTCAGTGGAAACAGGACATTTGGATGGAGTATTTATGC
ATAAGCGAGCTCAAAGGTTAAAGTTTCTATGTGAAAGAAATGATAAGGTA
TTTTTTGCATCCGTGCGATCTGGAGGAAGTAGCCAAGTGTTTTTCATGAC
CCTCAACAGAAATTCCATGATGAACTGGTAA
```

SEQ ID NO:2
MASDSPARSLDEIDLSALRDPAGIFELVELVGNGTYGQVYKGRHVKTGQL
AAIKVMDVTGDEEEEIKQEINMLKKYSHHRNIATYYGAFIKKNPPGMDDQ
LWLVMEFCGAGSVTDLIKNTKGNTLKEEWIAYICREILRGLSHLHQHKVI
HRDIKGQNVLLTENAEVKLVDFGVSAQLDRTVGRRNTFIGTPYWMAPEVI

-continued

ACDENPDATYDFKSDLWSLGITAIEMAEGAPPLCDMHPMRALFLIPRNPA
PRLKSKKWSKKFQSFIESCLVKNHSQRPATEQLMKHPFIRDQPNERQVRI
QLKDHIDRTKKKRGEKDETEYEYSGSEEEEEENDSGEPSSILNLPGESTL
RRDFLRLQLANKERSEALRRQQLEQQQRENEEHKRQLLAERQKRIEEQKE
QRRLEEQQRREKELRKQQEREQRRHYEEQMRREEERRRAEHEQEYURRQ
LEEEQRQLEILQQQLLHEQALLLEYKRKQLEEQRQAERLQRQLKQERDYL
VSLQHQRQEQRPVEKKPLYHYKEGMSPSEKPAWAKEVEERSRLNRQSSPA
MPHKVANRISDPNLPPRSESFSISGVQPARTPPMLRPVDPQIPHLVAVKS
QGPALTASQSVHEQPTKGLSGFQEALNVTSHRVEMPRQNSDPTSENPPLP
TRIEKFDRSSWLRQEEDIPPKVPQRTTSISPALARKNSPGNGSALGPRLG
SQPIRASNPDLRRTEPILESPLQRTSSGSSSSSSTPSSQPSSQGGSQPGS
QAGSSERTRVRANSKSEGQPVLPHEPAKVKPEESRDITRPSRPASYKKAI
DEDLTALAKELRELRIEETNRPMKKVTDYSSSSEESESSEEEEDGESET
HDGTVAVSDIPRLIPTGAPGSNEQYNVGMVGTHGLETSHADSFSGSISRE
GTLMIRETSGEKKRSGHSDSNGFAGHINLPDLVQQSHSPAGTPTEGLGRV
STHSDTPEIRTEYGMGSSTKASFTPFVDPRVYQTSPTDEDEEDEESSAAA
LFTSELLRQEQAKLNEARKISVVNVNPTNIRPHSDTPEIRKYKKRFNSEI
LCAALWGVNLLVGTENGLMLLDRSGQGKVYNLINRRRFQQMDVLEGLNVL
VTISGKKNKLRVYYLSWLRNRILHNDPEVEKKQGWITVGDLEGCIHYKVV
KTERIKFLVIALKNAVEIYAWAPKPYHKFMAFKSFADLQHKPLLVDLTVE
EGQRLKVIFGSHTGFHVIDVDSGNSYDIYIPSHIQGNITPHAIVILPKTD
GMEMLVCYEDEGVYVNTYGRITKDVVLQWGEMPTSVAYIHSNQIMGWGEK
AIEIRSVETGHLDGVFMHKRAQRLKFLCERNDKVFFASVRSGGSSQVFFM
TLNRNSMMNW

SEQ ID NO:3
TTTATGGCATTTAAGTCTTTTGCAGATCTTCAGCATAAGCCTCTGCTCGT
TGACCTCACAGTAGAAGAAGGTCAAAGGTTAAAGGTCATTTTTGGCTCAC
ACACTGGTTTCCATGTAATTGATGTTGACTCTGGAAACTCCTACGATATC
TATATACCATCCCATATTCAGGGTAATATCACTCCTCACGCTATCGTCAT
CTTGCCTAAAACAGACGGAATGGAGATGCTTGTCTGCTATGAGGATGAGG
GGGTGTATGTGAACACCTATGGCCGGATCACTAAGGATGTGGTGCTCCAA
TGGGGAGAAATGCCCACATCTGTGGGTAGGTTAACCATTCCTTATCTCCT
TCAGCAGTTCCACCCCCCAAATGAAACGAAGGGCAAGAAATGTGAAACAA
CCATTTGAGTTCACAAAAAAAAAA

SEQ ID NO:4
FMAFKSFADLQHKPLLVDLTVEEGQRLKVIFGSHTGFHVIDVDSGNSYDI
YIPSHIQGNITPHAIVILPKTDGMEMLVCYEDEGVYVNTYGRITKDVVLQ
WGEMPTSVGRLTIPYLLQQFHPPNETKGKKCETTI

SEQ ID NO:5

```
GCAAGCCTGCCATAGACACAGCAGGCACCAACAAGTCAGATTTTAG
GGAACCTGAAGGCAAGGCTTTGACAAAATTCTAAGATTCCAATCAT
GTTATGTTCCTCCAAACTTCCCAACATACTGTTAACAACATCTGTG
CAGAGATGTGTATGTATTTAGTTCAGGTTGACTTGTGTCCTTATAG
AAACCCTTACTCGAATGATTTGAACCTTTATGTGACTGACTGGGAT
TTTCCCCAAAGCTCCAAGCATGGCCGCCTATGGTATCCAGGTGTTG
CAAAATGGTATCTGTGCTGTGCTTCCTGTTTTAACCTACCTCGTTT
TGTTTGWTTTTGTTTCTCTGTTCATCACAGCAGKGTTATCTCCAGG
AGACATATARAGAGCTCACCCGGCAATCTCAAGCTGKCTTGAACAT
TTTCAAAACAAGTAGTTGACCAAATTCTTYTTTAAAAAATTGGAGR
GGAGAAAATAAAATCTCCAATGACAAGAAACTAATGCRAGCTATTT
TTGAAAGAAATGCAAWTTACTGGTAAATGGATCAAAAAAGAAAGAC
AAAAACCCGTGCCTHTCCTGAWCTTKGCCTAAACAAATGAGCAGCT
GAGTTCTATTAATGAGAACGAAACACATGTTAGGAAAACGGTACCT
TTTTAATCTGGTGGTTGGCCAAAGGGGATGAGAAAGAGAACTATTC
TGAGTTCTGGACTANGGTGAATCTGGTAATCCCCAAAGGGTGATTG
KTATTTGTAGTTATCTGAAGCAGGNTAACACACAGAAATCCAGTGA
GGGTGGTCTTCAAGTGATCACCAGGATGTGTCCATCATGGCCCCTC
TAGCTCTCAAAGGCAATGAAATCCTCCCGTTCTCATTTTTACTGCT
GGGGTTATGCTGCCGAACAACACTGTCCTTACGAATTCCACAGGAC
AAATTCAGCAATAGCTCTGGGTTGAATTTAGCGACTACAATAATTG
GATGCCGATGCCGACAAAAATAATATGGATTTGGGTCTTGTCTCCA
AATGTGGTTGCCACCAGCTCTTTATATCACTGCTGTGATGTTTTCA
ACCTGAGGCTTCTTTAAATTACGTTGCAAACTGATCTTTTGTCTTT
ATGTTTCGTGCCACTTTGTTCTTACTTCTAAGCGTACATCTGAAAC
ACACAGCTTTAAATGATTTTTTTATTGTGGGACTTTGGGTACAGTT
AAGAAATAAAAGGGAATCATTGTGTTTAAACATAAGGTAGTTTGTG
AATGTATTTTTTAAAATCTAGATTCATTGGAACAAGAAAACCATAA
GAAAACATATTAATGCCGTCTTGTTTACAGTATGGACAGTGGCATA
ACATTACATGAGCTTTTTCTGGTGCCAACAAAATAAAAACAGACGT
TAAACATCAAAAAAAAAAAA
```

In the figures

FIG. 1 Time course TaqMan™ analysis of KIAA0551 mRNA induction in rat Dorsal Root Ganglia in response to a partial sciatic ligation, a model for increased sensitivity to somatic pain. a) mRNA induction expressed as number of copies of KIAA0551 per ng of RNA. b) mRNA induction expressed relative to the expression of cyclophilin mRNA, a housekeeping gene used as an internal standard.

Figure 2:
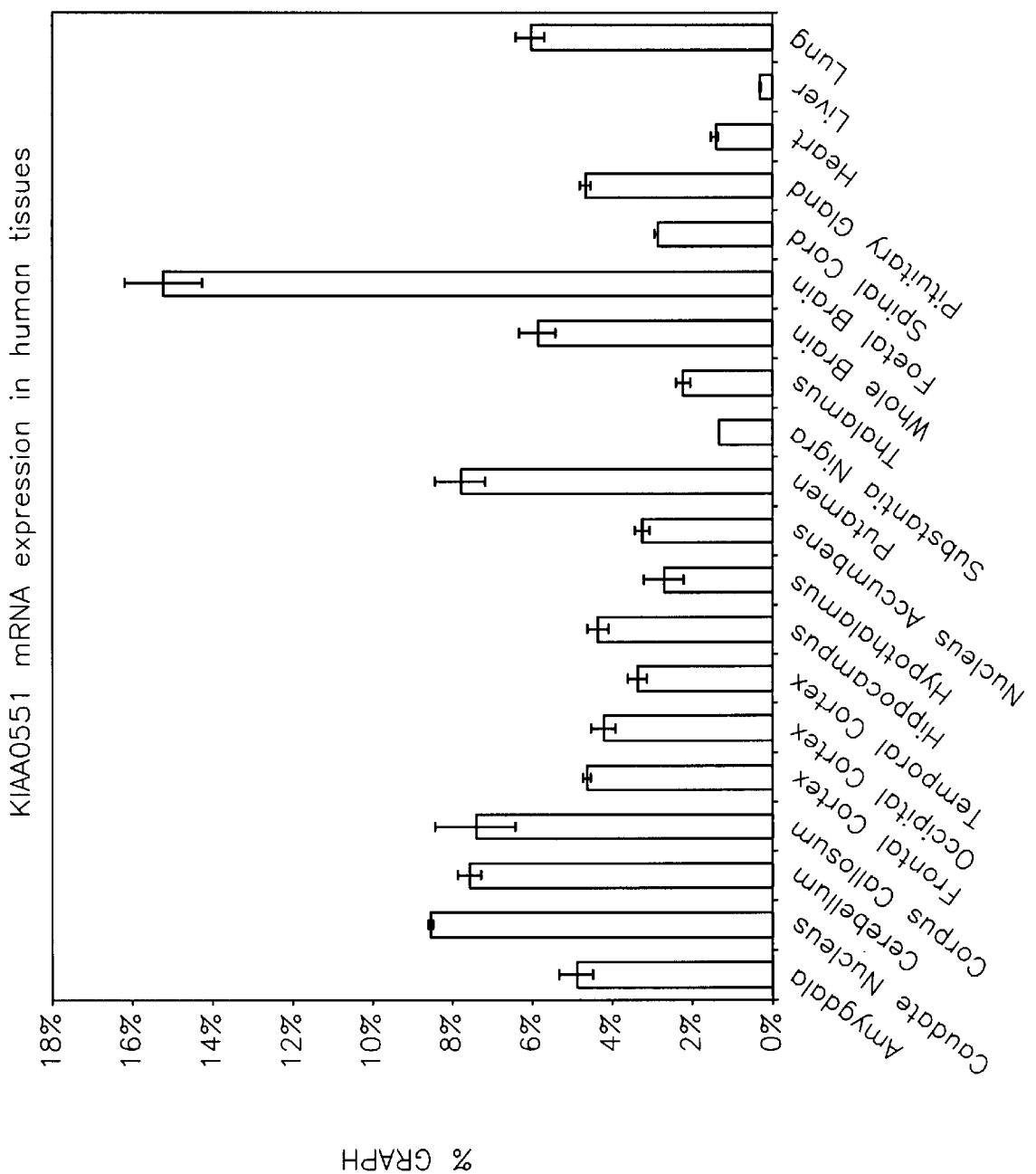

FIG. 2 TaqMan™ expression profile of KIAA0551 mRNA in human CNS and peripheral tissues, expressed relative to the expression of GAP-DH mRNA, a housekeeping gene used as an internal standard.

FIG. 3. Overexpression of full-length NAK protein in HEK293 cells. Lane1: pcDNA3.1hismyc transfected cells. Lane 2: pcDNA3.1 NAK transfected cells. NAK migrates as a 190 kDa protein; the smaller band could represent a cleaved product. Protein was visualized using anti-myc (9E10) antibodies which recognizes the myc-epitope tag of the recombinant protein and ECL FIG. 4. NAK is an enzymatically active kinase and can be assayed on myelin basic protein (MBP). a) Assay of MBP kinase activity in anti-myc (9E10) immunoprecipitates from recombinant NAK-transfected HEK293 cells compared to control transfected cells. b) Comparison of MBP kinase activity of full-length recombinant NAK, and two C terminal truncates encoding amino acid residues 1–337 (NAK1–337) or 1–529 (NAK 1–529). Experiment was controlled for equal expression of recombinant NAK proteins.

---

What is claimed is:

1. An isolated polynucleotide comprising a polynucleotide sequence encoding the polypeptide of SEQ ID NO: 2.

2. An isolated polynucleotide comprising the polynucleotide sequence of SEQ ID NO: 1.

3. An expression vector comprising a polynucleotide capable of producing a polypeptide comprising the amino acid sequence of SEQ ID NO: 2 when said expression vector is present in a compatible host cell.

4. A host cell comprising the expression vector of claim 3.

5. A process for producing a polypeptide comprising the step of culturing a host cell as defined in claim 4 under conditions sufficient for the production of said polypeptide and recovering the polypeptide from the culture medium.

* * * * *